US008235929B2

(12) United States Patent
Griffin

(10) Patent No.: US 8,235,929 B2
(45) Date of Patent: Aug. 7, 2012

(54) METHOD OF TREATING PRURITIS

(76) Inventor: Santea B. Griffin, Durham, NC (US)

( * ) Notice: Subject to any disclaimer, the term of this patent is extended or adjusted under 35 U.S.C. 154(b) by 469 days.

(21) Appl. No.: 12/500,275

(22) Filed: Jul. 9, 2009

(65) Prior Publication Data

US 2011/0008411 A1    Jan. 13, 2011

Related U.S. Application Data

(60) Provisional application No. 61/080,748, filed on Jul. 15, 2008.

(51) Int. Cl.
| A61L 15/00 | (2006.01) |
| D04B 7/16 | (2006.01) |
| A61F 5/08 | (2006.01) |
| A61F 13/15 | (2006.01) |
| A61F 13/00 | (2006.01) |

(52) U.S. Cl. .. 602/75; 66/202; 606/204.15; 604/385.01; 128/891; 424/443

(58) Field of Classification Search ............... 602/75, 602/60, 41; 604/385.01, 387, 385.04; 128/891, 128/889; 424/400, 443, 402; 606/131, 204.15; 15/227; 66/202; 139/35
See application file for complete search history.

(56) References Cited

U.S. PATENT DOCUMENTS

| 3,339,546 A | 9/1967 | Chen |
| 3,428,043 A | 2/1969 | Sheperd |
| 3,598,122 A | 8/1971 | Zaffaroni |
| 3,895,652 A | 7/1975 | Zach |
| 3,972,328 A | 8/1976 | Chen |
| 4,307,717 A | 12/1981 | Hymes |
| 4,399,816 A | 8/1983 | Spangler |
| 4,641,643 A | 2/1987 | Greer |
| 4,655,768 A | 4/1987 | Marecki |
| 4,726,364 A | 2/1988 | Wylan |
| 4,776,331 A | 10/1988 | Simjian |
| 4,880,416 A | 11/1989 | Horiuchi |
| 5,031,247 A * | 7/1991 | Carter ............................... 2/242 |
| D342,790 S | 12/1993 | Zona |
| 5,352,216 A | 10/1994 | Shiono |
| 5,375,262 A | 12/1994 | Carter |
| 5,413,780 A | 5/1995 | Huprich |
| 5,429,590 A | 7/1995 | Saito |
| 5,683,354 A | 11/1997 | Levy |
| 5,692,937 A | 12/1997 | Zhang |
| 5,735,807 A | 4/1998 | Cropper |
| 5,741,510 A | 4/1998 | Rolf |
| 5,745,921 A | 5/1998 | Mitchell |
| 5,820,578 A | 10/1998 | Johansen |
| 5,840,072 A | 11/1998 | Carey |
| 5,876,365 A | 3/1999 | Hart |
| 5,947,917 A | 9/1999 | Carte |
| 5,948,433 A | 9/1999 | Burton |
| 6,000,402 A | 12/1999 | Able |
| 6,004,345 A | 12/1999 | Sudsina |
| 6,262,330 B1 | 7/2001 | Fujisawa |
| 6,297,421 B1 | 10/2001 | Kitazaki |
| 6,469,227 B1 | 10/2002 | Cooke |

(Continued)

*Primary Examiner* — Patricia Bianco
*Assistant Examiner* — Tarla Patel
(74) *Attorney, Agent, or Firm* — James G. Passé; Passé Intellectual Property, LLC

(57) ABSTRACT

The present invention relates to a method of treating dermatologic pruritis. The skin involved with purities is covered with an organic cloth in order to make it more difficult to scratch. The contact of the organic cloth not only makes it difficult to scratch but adds a soothing feel thus lessening the tendency to need to scratch.

5 Claims, 4 Drawing Sheets

U.S. PATENT DOCUMENTS

| | | |
|---|---|---|
| 6,488,643 B1 | 12/2002 | Tumey |
| 6,525,238 B2 | 2/2003 | Corrales |
| 6,660,901 B2 | 12/2003 | Church |
| 6,763,525 B1 | 7/2004 | Spector |
| 6,830,758 B2 | 12/2004 | Nichols |
| 7,048,706 B2 | 5/2006 | Cea |
| 2001/0031939 A1 | 10/2001 | McTamney |
| 2003/0023196 A1 | 1/2003 | Liguori |
| 2003/0023197 A1 | 1/2003 | Liguori |
| 2005/0010154 A1 | 1/2005 | Wright |
| 2005/0107728 A1 | 5/2005 | Vetters |
| 2006/0293736 A1 | 12/2006 | Mario, Jr. |

* cited by examiner

METHOD OF TREATING PRURITIS

This application claims priority of provisional application No. 61/080,748 filed on Jul. 15, 2008 and is incorporated herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to a method of treating a dermatologic pruritis. In particular the method comprises the covering of the skin with an organic material to relieve the pruritis and make it more difficult to scratch the afflicted skin area.

2. Description of Related Art

Pruritis, with an accompanying itch of a portion of the skin, can come from a number of different causes. Examples include eczema, urticaria, contact dermatitis, atopic dermatitis, dermatitis herpetiformis, psoriasis, lichen planus, rhus dermatitis, biliary obstruction, uremia, lymphoma, leukemia, polycythemia vera, dry skin, poison ivy, ring worm and the like.

Treatment of the itch associated with these conditions is difficult and frustrating. Frequently, even with treatment, the act of scratching continues often with damage to the skin being scratched. While the delivery of medicaments to an affected area is possible, frequently with children, infants or the like, such treatments are not appropriate. In addition, many adults avoid the use of medicaments whenever possible.

A number of protective barriers are in the art, however, they are essentially designed to be used with anti-pruritics. They usually have an adhesive type backing in which the adhesive can further irritate an already inflamed skin area. While these barriers also allow the prevention of touching the affected area, the use of medicaments and adhesives is less than ideal.

Accordingly, a method of reducing the ability to scratch a particular pruritic skin condition without all the problems associated with prior patches is desirable and missing from the current art.

BRIEF SUMMARY OF THE INVENTION

The present invention relates to the discovery that positioning a piece of organic silk or cotton over a portion of skin affected with an pruritic itch allows the user to be relieved of some itch and lessens the ability of the individual to scratch the skin and cause damage to the affected area.

Accordingly, one embodiment of the present invention relates to a method of treating a pruritic itch on an individual's skin consisting of:
  a) positioning a piece of cloth over at least a portion of the affected skin, the cloth consisting of organic silk or cotton; and
  b) affixing the cloth at the positioned location by a means selected from the group consisting of compression and self fastening.

In yet another embodiment, the present invention relates to an article for treating pruritic itch on an area of an individual's skin consisting of a piece of organic silk or cotton cloth of sufficient size to cover the area of an individual's skin and a means to hold the cloth on the skin without attaching it directly to the skin.

As can be readily seen, the present invention is easy to use and avoids the use of a medicament in treating the individual, such as a child affected with a pruritic itch.

DETAILED DESCRIPTION OF THE INVENTION

Figure 1A:
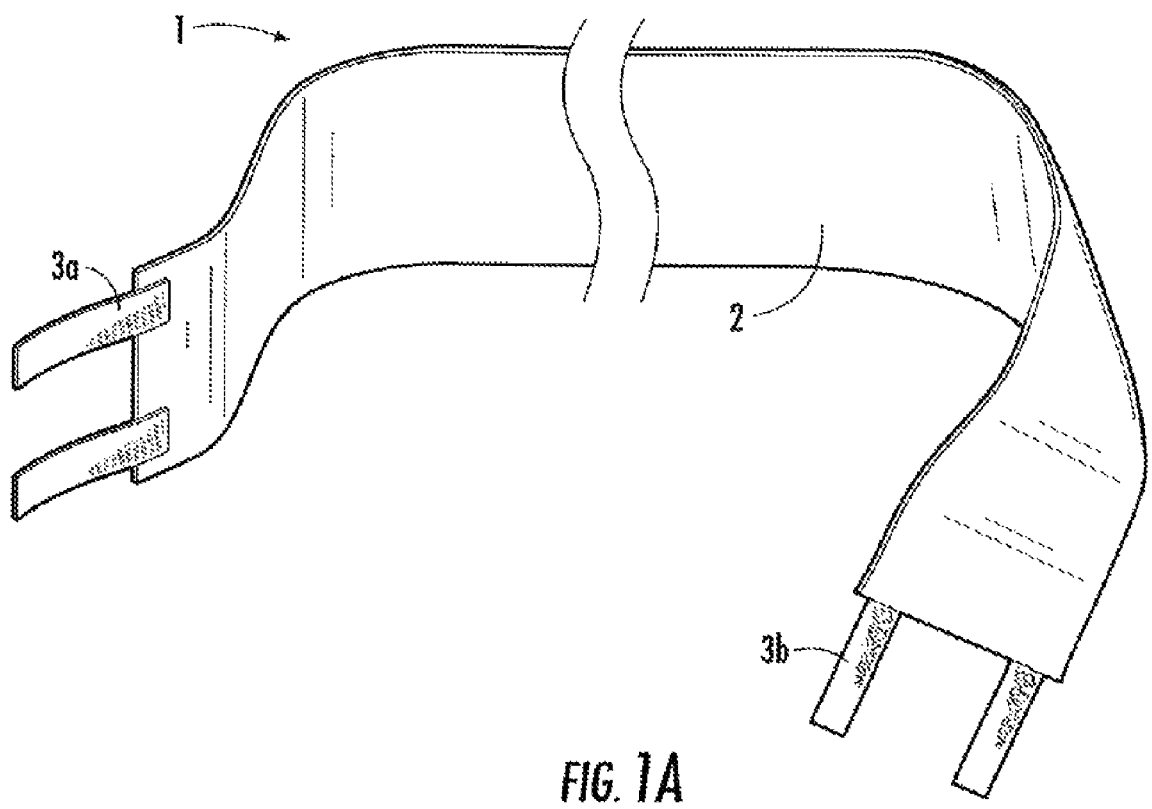
FIG. 1a is a top view of a wrap with Velcro® closures.

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein, and specifically describes embodiments in order for those skilled in the art to practice the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein "treating a pruritic itch on an individual's skin" refers to having an itch caused by a disease or other cause (as described above) such that a reduction in the ability to scratch the itch would be a useful treatment. It does not refer to medically treating the cause of the itch, rather it deals solely with treating the itch.

As used herein "cloth" refers to 100% organic cotton or silk. It has been discovered that positioning a piece of cloth of one of these two materials greatly reduces the need to scratch and reduces the ability to scratch the area, thus leading to quicker healing and less skin damage. The particular piece of cloth will be thick enough to prevent the general scratching. Such thickness can be determined and may be different from individual to individual, however, one skilled in the art could easily determine the optimum thickness (or layers of cloth) necessary to achieve the desired results taught herein. In general the shape of the cloth will be of a size and shape to cover the dermatologic problem to be treated or slightly larger to prevent any shifting of the cloth from exposing affected skin.

Once the piece of cloth is positioned on the particular portion of skin to be "treated" it must be held in place. The cloth is "affixed," that is, it is positioned in the desired location by a means that does not attach to the skin. For example, means for attaching the cloth could be by compression such as would be the case for a tubular article. The cotton or silk has enough give to it that a size slightly smaller than the limb that it will be used on allows the article to be slipped over the leg or arm and held in place because of the small size in relationship to the diameter of the individual's limb the article is being used on. Also, self fastening means are within the contemplation of the present invention. The term "self fastening" means that an article can be wrapped or positioned and then attach to itself. For example, Velcro® of both male and female parts could be attached to the cloth in such a way that the Velcro® parts mate when the cloth is being affixed. Similarly a strap or clips like used for compression bandages like "Ace® bandages," could be used. Likewise, the item could be wrapped or positioned and sewn, such as by using laces or needle and thread to hold in place.

The positioning of the article of the present invention promotes healthy skin by preventing fierce scratching which can rip the skin and cause more harm such as an infection. The skin can then heal. The device helps hold moisture and provides comfort especially to children to whom the device is especially useful.

Now referring to the drawings, FIG. 1a is a top view of a wrap with Velcro® closures. The article for treating pruritic itch 1 is comprised of a cloth portion 2 comprised of either 100% organic cotton, silk or a combination of the two. The embodiment in this view is wrapped around the particular skin area and closed using the Velcro® male 3a and Velcro® female 3b closure straps.

Figure 1B:
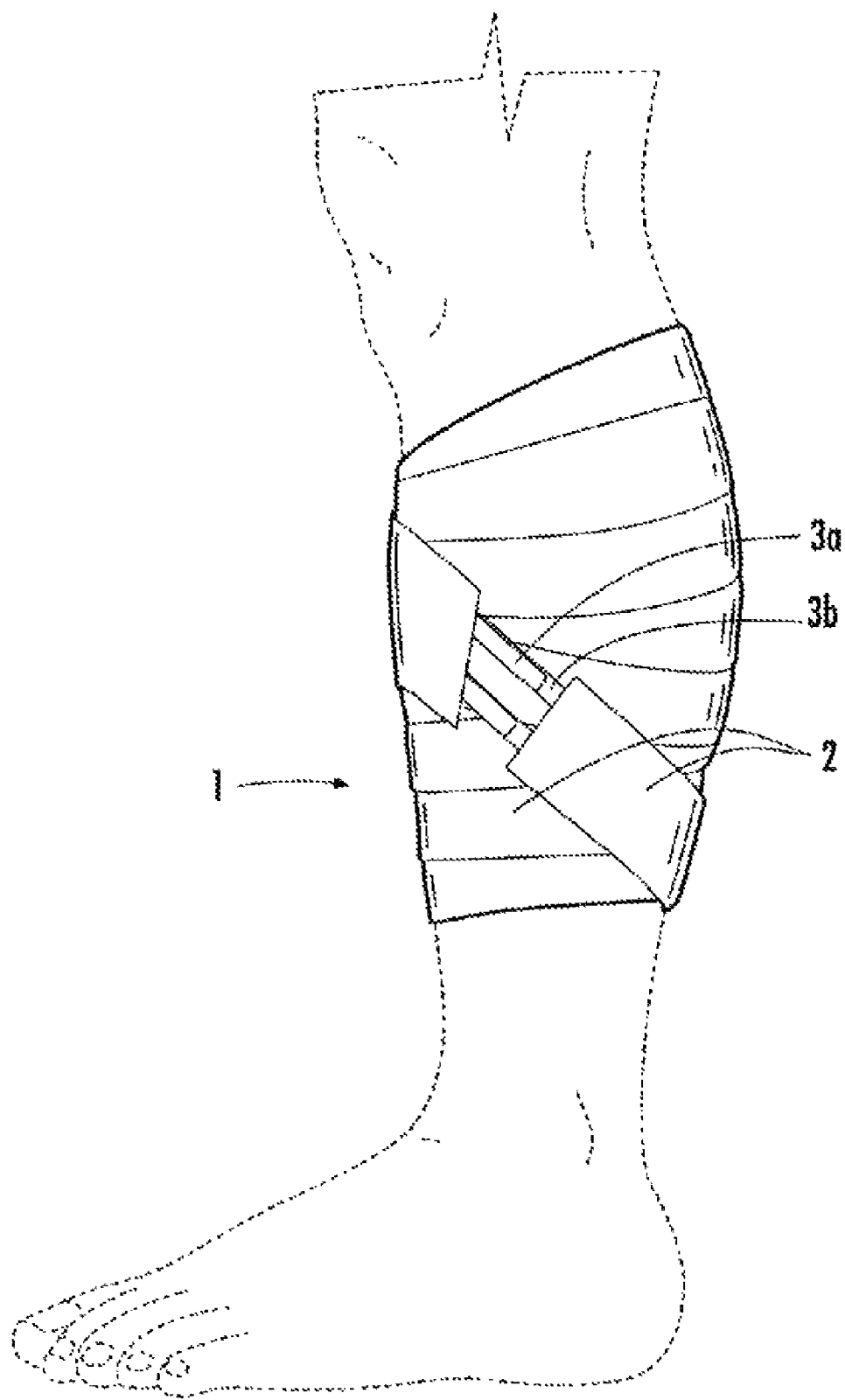
FIG. 1b is the wrap of FIG. 1a applied to the leg of an individual.

FIG. 1b depicts a perspective view of the article of FIG. 1a wrapped around the calf of an individual and closed with the Velcro® closures 3a and 3b. It would be assumed the area of itch is beneath the area. The article is wrapped around the affected area with Velcro®, although, clips and straps could also be used.

Figure 2A:
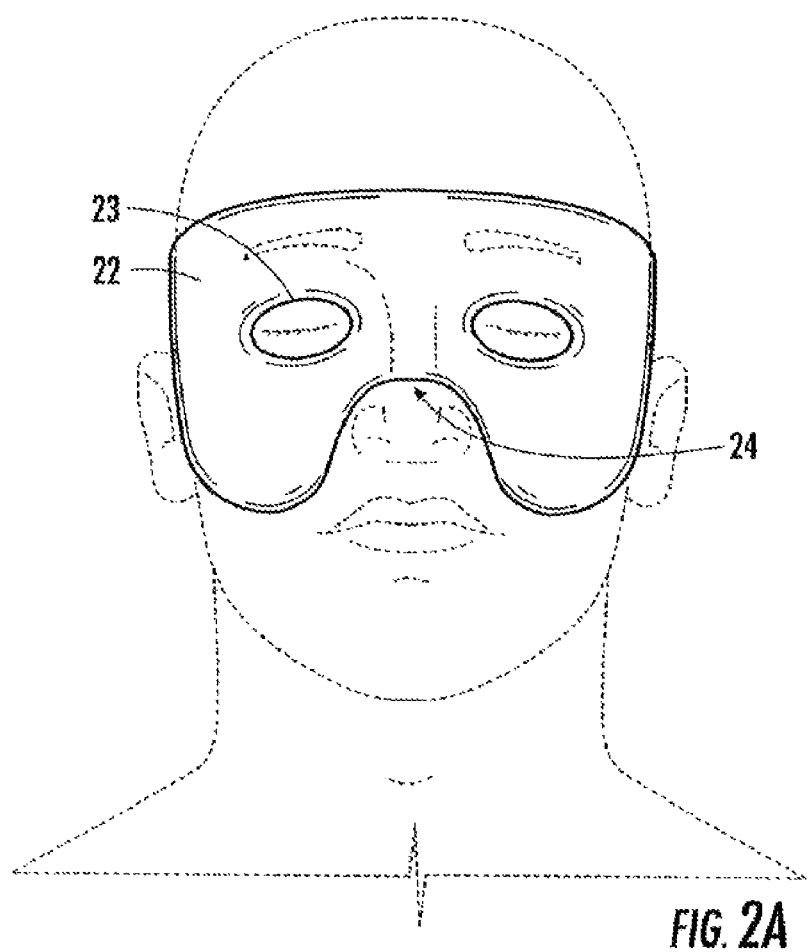
FIG. 2a is a front view of an article of the present invention for treating the facial area.
Figure 2B:
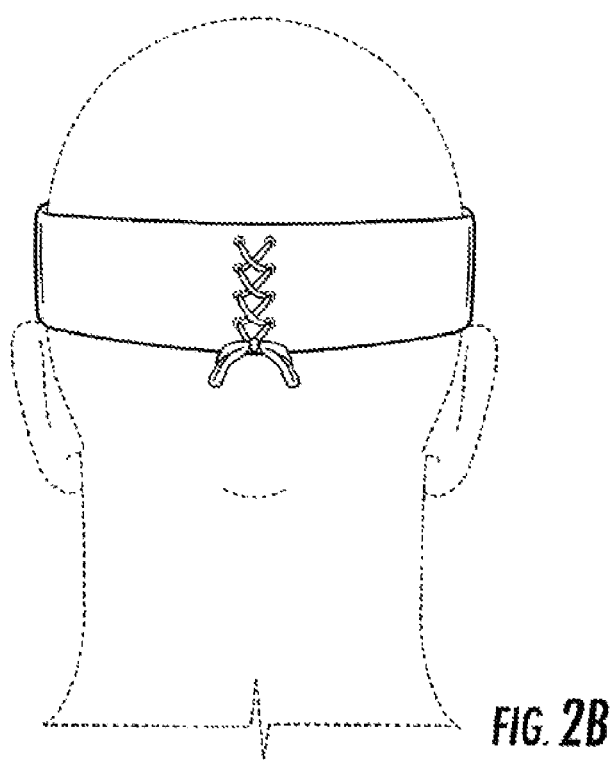
FIG. 2b is the FIG. 2a article back view depicting the lace-up (sewing) type closure.

FIGS. 2a and 2b are views of the front and back respectively of a device of the present invention designed to apply to the facial area of an individual. Face mask 22 with eye holes 23 is positioned on the facial area with nose cutout 24 designed to allow the nose to breath. The article wraps around the individual's head and is tightened in the back side as in FIG. 2b with sew up lacing (like a pair of shoes).

Figure 3:
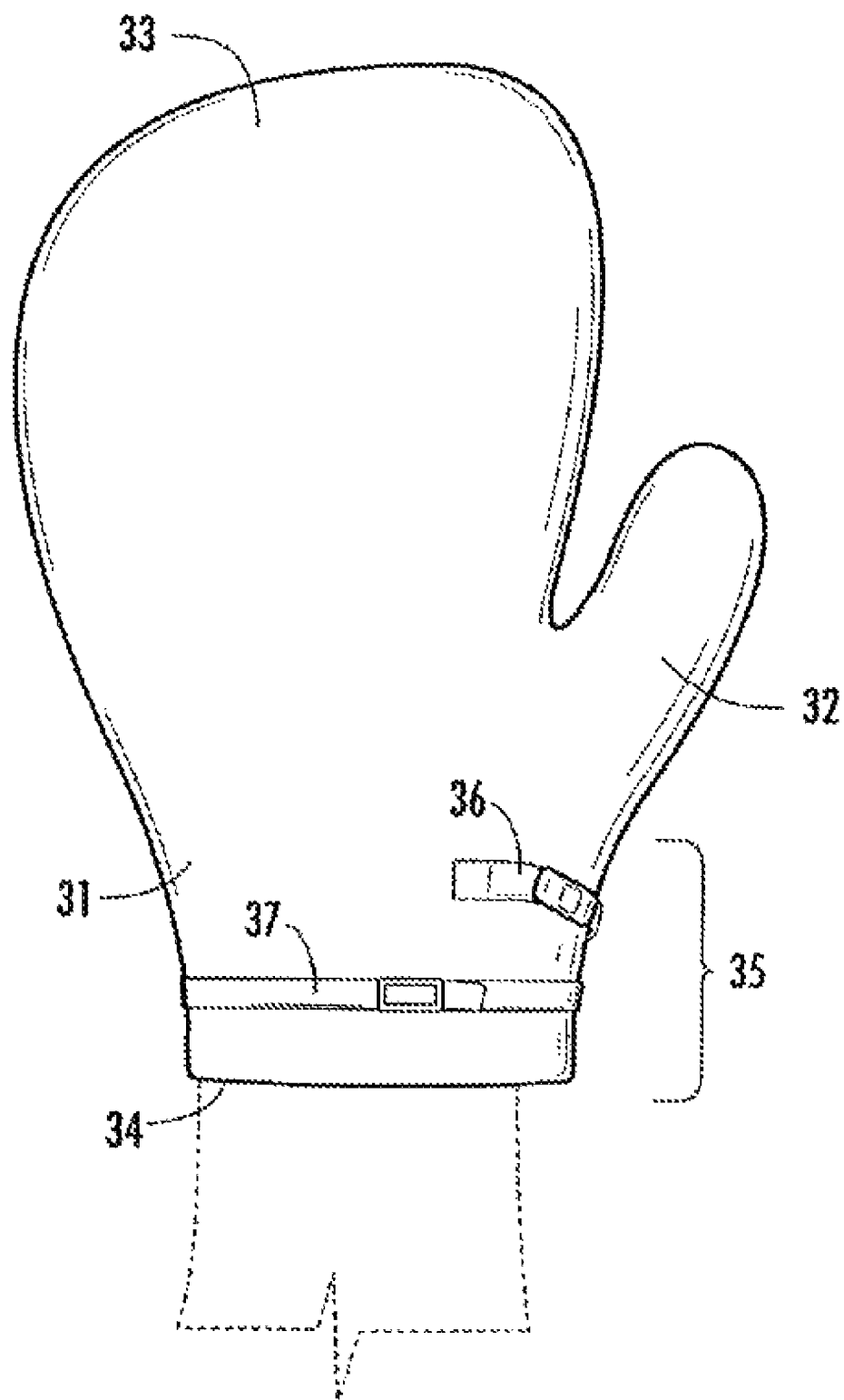
FIG. 3 depicts an article in the shape of a mitt where closure is accomplished by both a strap and a clip.

FIG. 3 is an article for covering the hand of an individual having an itch. Mitt 31 comprises a thumb area 32 and a finger area 33. The wrist area 34 is relatively open and allows the user's hand to slip into the mitt 31. In order to keep the mitt 31 in place, the mitt 31 can be tightened around the wrist area 34 by use of either/or clip 36 or strap 37.

The embodiments and suggestions of the scope of the invention are not to be interpreted as limiting or the only way to practice the invention. Changes to where on the body the device is used the method of applying it within the scope of the invention is clear to one skilled in the art in view of the disclosure herein. Accordingly, the claims which follow should not be limited.

What is claimed is:

1. A method of treating a pruritic itch on an individual's skin consisting of:
    a) positioning a piece of cloth over at least a portion of the affected skin, the cloth consisting of organic silk or organic cotton; and
    b) affixing the cloth at the positioned location by a means selected from the group consisting of compression and self fastening.

2. A method according to claim 1 wherein the method of affixing is compression.

3. A method according to claim 2 wherein the piece of cloth has a stretch and is tubular shaped to fit on an individual's affected limb.

4. A method according to claim 1 wherein the piece of cloth is self fastened.

5. A method according to claim 4 wherein the piece of cloth is self fastened by hook and loop fastener, straps, sewing or clips attached to the cloth.

* * * * *